US006312905B1

(12) United States Patent
Liu et al.

(10) Patent No.: US 6,312,905 B1
(45) Date of Patent: Nov. 6, 2001

(54) METHOD FOR DETECTING MUTATIONS IN NUCLEIC ACIDS

(75) Inventors: Qiang Liu, Upland; Steve S. Sommer, Duarte, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/475,156

(22) Filed: Dec. 30, 1999

Related U.S. Application Data

(60) Provisional application No. 60/114,579, filed on Dec. 31, 1998.

(51) Int. Cl.[7] .............................. C12Q 1/68; C12P 19/34; G01N 33/00; C07H 19/207; C07H 5/06
(52) U.S. Cl. ................................ 435/6; 435/91.2; 436/94; 436/501; 536/26; 536/27; 536/28; 536/29; 935/77; 935/78
(58) Field of Search ....................... 435/6, 91.2; 536/22.1

(56) References Cited

U.S. PATENT DOCUMENTS 5,124,247 * 6/1992 Ansorge .................................. 435/6

OTHER PUBLICATIONS

Myers et al., "Detection of single base substitution in total genomic DNA", Nature, vol. 313, pp. 495–498, Feb. 1985.*
Grossman et al., "High–Density Multiplex Detection . . . ", Nucleic Acids Research, vol. 22(21), pp. 4527–4527–4534, Aug. 1994.*
Qiang Liu et al., "Denaturation Fingerprinting: Two Related Mutation Detection Methods Especially Advantageous for High G+C Regions," Bio Techniques, 24:140–147 (Jan. 1998).

Blaszyk, H., et al., "Rapid and efficient screening for p53 gene mutations by dideoxy fingerprinting (ddF)", Bio Techniques, 1995, 18:256–260.
Haavik, J., et al., "Bi–directional dideoxyy fingerprinting (Bi–ddF): rapid and efficient screening for mutations in the Big Blue transgenic mouse mutation detection system", Bio Techniques, 1996, 20:988–994.
Innis, M.A. et al., "DNA sequencing with Thermus aquaticus DNA polymerase and direct sequencing of polymerase chain reaction–amplified DNA", Proc. Natl Acad. Sci. USA, 1988, 85:9436–9440.
Liu, Q., et al., "Bidirectional dideoxy fingerprinting (Bi–ddF): a rapid method for quantitative detection of mutations in genomic regions of 300–600 bp", Hum. Mol. Genet., 1996, 5:107–114.

(List continued on next page.)

Primary Examiner—Jeffrey Fredman
Assistant Examiner—Arun Chakrabarti
(74) Attorney, Agent, or Firm—Rothwell, Figg, Ernst & Manbeck

(57) ABSTRACT

A denaturation fingerprinting method (dnF) involves subjecting a nucleic acid segment of interest to bidirectional cycle sequencing using oppositely oriented primers and incorporating two different dideoxynucleotides (ddNTPs) in the sequencing reaction. The resulting fragments are separated by denaturing electrophoresis. In one embodiment, designated $dnF_{2R}$, reactions and electrophoretic separation using the two ddNTPs are conducted separately. In an alternative embodiment, designated $dnF_{1R}$, one of the ddNTPs has a mobility altering modification such that electorphoretic separation occurs when both ddNTPs are employed in the same reaction. The methods are useful for detecting genetic mutations.

2 Claims, 3 Drawing Sheets

OTHER PUBLICATIONS

Liu, Q., et al., "Parameters affecting the sensitivities of dideoxy fingerprinting and SSCP", *PCR Methods Appl.* 1994, 4:97–108.

Livak, K.J., et al., "Detection of single base differences using biotinylated nucleotides with very long linker arms", *Nucleic Acids Res.*, 1992, 20:4831–4837.

Orita, M., et al., "Detection of polymorphisms of human DNA by gel electrophoresis as single–strand conformation polymorphisms", *Proc. Natl. Acad. Sci. USA*, 1989, 86:2766–2770.

Prober, J.M., et al., "A system for rapid DNA sequencing with fluorscent chain–terminating dideoxynucleotides", *Science*, 198, 238:336–341.

Sarkar, G., et al., "Access to an mRNA sequence or its protein product is not limited by tissue or species specificity", *Science*, 1989, 244:331–334.

Sarkar, G., et al., "Dideoxy fingerprinting (ddF): a rapid and efficient screen for the presence of mutations", *Genomics*, 1992, 13:441–443.

Sommer, S.S., et al., "Phage promoter–based methods for sequencmg and screening for mutations", The Polymerase Chain Reaction, K. Mullis, F. Ferre and R.A. Gibbs (Eds), Birkhauser, Boston, 1994, 214–221.

Weinshenker, B.G., et al., "Genetic variation in the tumor necrosis factor cs gene and the outcome of multiple sclerosis", *Neurology*, 1997, 49:378–385.

Yoshitake, S., et al., "Nucleotide sequence of the gene for human factor IX (anti–hemophilic factor B)", *Biochemistry*, 1985, 24:3736–3750.

* cited by examiner

METHOD FOR DETECTING MUTATIONS IN NUCLEIC ACIDS

This application claims priority from provisional patent application Ser. No. 60/114,579, filed Dec. 31, 1998.

BACKGROUND OF THE INVENTION

Mutation scanning methods are important for elucidating the genetic basis of human disease. Single-stranded conformation polymorphism (SSCP)(7) (a bibliography is provided at the end of the written description) is the most widely used mutation scanning method, but its sensitivity varies. Two hybrids between SSCP and Sanger dideoxy sequencing have been developed. These hybrid methods can detect the presence of virtually all mutations. The first hybrid method is dideoxy fingerprinting (ddF). A Sanger reaction is performed with one dideoxy terminator and with one primer to produce a nested set of 5' co-terminal DNA segments, then the segments are denatured and electrophoresed through a non-denaturing gel (10). Mutations can be detected by an alteration in the mobility of at least one of the multiple termination segments that contain the mutation (informative SSCP component). In addition, 6 out of 12 types of possible single-base substitutions result in a gain and/or loss of a dideoxy termination segment at the mutation site (informative dideoxy component). In manual gels, ddF can detect virtually all mutations in a 300-bp region of DNA (1,5,10). The second hybrid method, bidirectional ddF (Bi-ddF) is a modification of ddF in which a cycle sequencing is performed with opposite primers to scan simultaneously for mutations in both directions. Bi-ddF has two important advantages over ddF: (i) the dideoxy component can detect 10 out of 12 types of possible single-base substitutions, and (ii) the SSCP component is on the average more informative because alterations of mobility can be detected in either the downstream or upstream direction. As a result, Bi-ddF can screen 600-bp segments with virtually 100% sensitivity (2,4). However, when these methods are adapted for high G+C regions, smearing of bands sometimes lowers the resolution.

SUMMARY OF THE INVENTION

In accordance with the present invention, a denaturation fingerprinting method ("dnf") comprises subjecting a nucleic acid segment to bidirectional cycle sequencing using oppositely oriented primers that bound the segment of interest, wherein two different dideoxynucleotides (ddNTPs) are employed in the sequencing reaction and separating the fragments by denaturing electrophoresis to produce a fingerprint pattern.

In one embodiment, designated $dnF_{2R}$, fingerprints are generated by performing denaturing gel electrophoresis on bidirectional cycle-sequencing reactions with each of two ddNTPs, e.g., ddATP and ddCTP. When the fingerprints are combined, all sequence changes are expected to result in one extra and one absent segment.

An alternative embodiment, designated $dnF_{1R}$, involves performing a single reaction with one ddNTP and a second chemically modified terminator (e.g., ROX-conjugated ddCTP), which retards the mobility of the same termination products, thus permitting resolution of fragments in a single electrophoresis lane.

Denaturation fingerprinting involves technology that is essentially identical to sequencing. Thus, the expertise in sequencing that many laboratories have can be applied directly to these methods. DnF is particularly advantageous for regions of high G+C content, such as promoter regions, because segments may smear when bi-ddF is performed in the absence of urea. However, substantial evidence indicates that increasing the urea concentration to 0.5 M for 60% G+C region and 1.5 M for 70% G+C regions resolves the problem without reducing the sensitivity at those G+C contents. While bi-ddF and dnF may involve the use of urea for high G+C segments bi-ddF utilizes the SSCP effect as the primary mechanism of detecting mutation, while dnF uses the dideoxy component as the primary mechanism of detecting mutations and the SSCP effect is the secondary mode of detecting mutations.

DETAILED DESCRIPTION OF THE INVENTION

In the denaturation fingerprinting method of this invention, Sanger dideoxy termination reactions are performed with two dideoxy terminators. Termination reactions are performed simultaneously in the downstream and the upstream directions. In $dnF_{2R}$, the two Sanger termination reactions are performed separately, electrophoresed separately and then analyzed. For example, if a bidirectional cycle-sequencing reaction is performed with ddATP, ten of the twelve possible types of mutations will produce an extra segment, an absent segment or both, as shown in Table 1, below. If the second bidirectional cycle-sequencing reaction with either ddCTP or ddGTP is performed, all twelve possible sequence changes will be associated with one absent and one extra segment when both fingerprints are examined. For example, with an A→G mutation, a segment is lost when ddATP is used in the downstream termination reaction, and a segment is gained when ddCTP is utilized in the upstream termination reaction. The observed sensitivity should parallel these theoretical values if shadow segments are not a major problem, and all termination segments occur at reasonable intensities. Unmodified ddNTPs are not combined in one reaction, because certain mutations would result in an absent and added base at the same site (Table 1). However, when one of the dideoxy nucleotides is modified so that the mobility is changed by at least 1 bp, all types of mutations can be detected in one reaction ($dnF_{1R}$). Any modification that cause a discernable shift in the mobility of fragments containing the modified ddNTP may be employed. ROX-conjugated ddCTP and FAM-conjugated ddATP retard the migration of DNA segments by two nucleotides (8), while incorporation of Biotin 11-dUTP, a commercially available analog of TTP, causes a one nucleotide mobility shift (6). Ideally, a modified nucleotide would retard mobility by one and a half or two and a half nucleotides, such that extra and absent segments due to the mutation are less likely to migrate identically to another segment (e.g., hexyethylene oxide).

Figure 1:
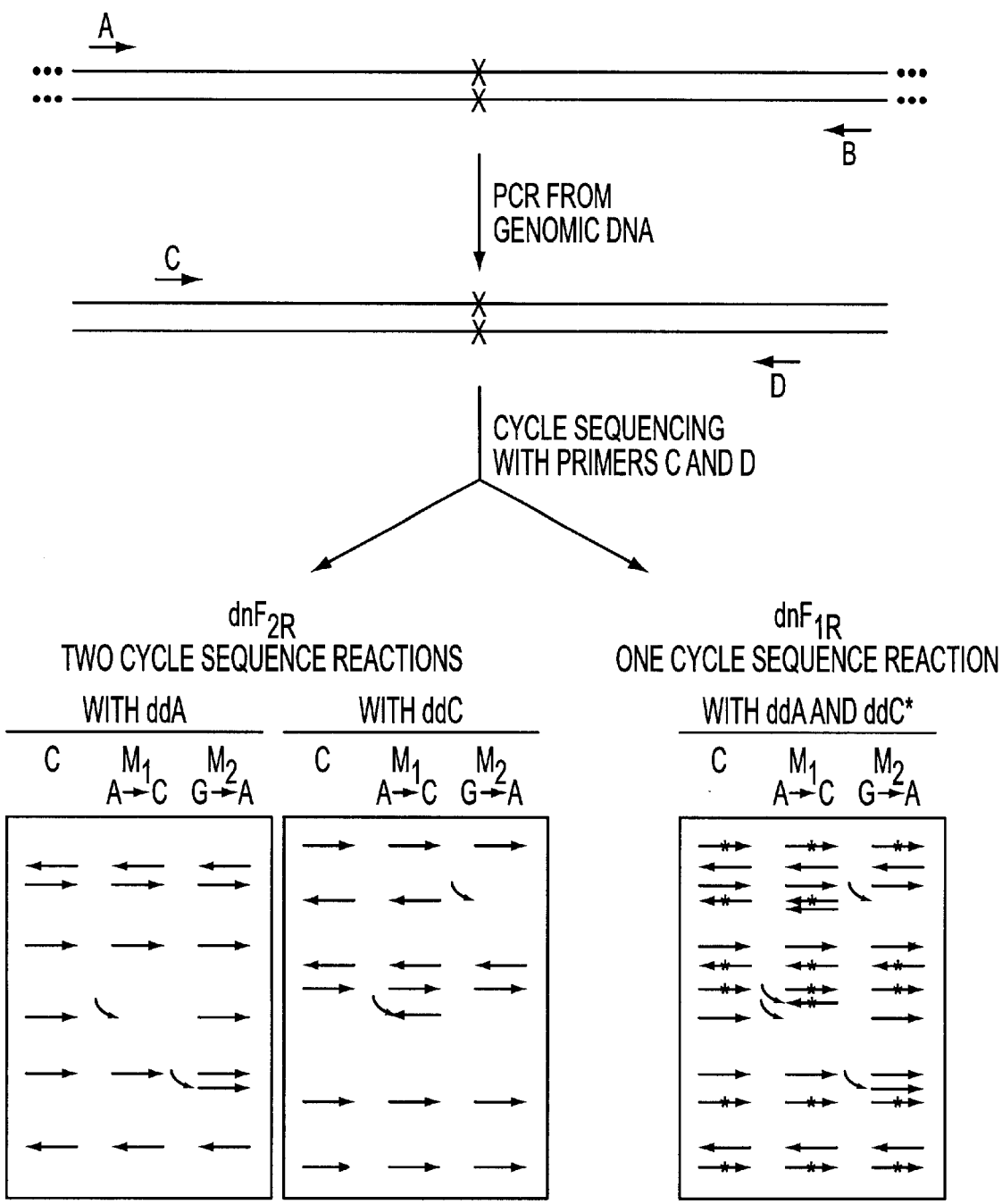
FIG. 1 is a schematic illustration of the denaturation fingerprinting methods of this invention.

FIG. 1 illustrates two embodiments of the denaturation fingerprinting method of this invention. The figure illustrates the initial PCR amplification of a nucleic acid segment, such as a genomic region of interest, using primers A and B. Taq cycle sequencing is performed with two opposite primers C and D followed by denaturing electrophoresis. For $dnF_{2R}$ (left), two ddNTP terminators are used separately in two reactions and then are electrophoresed through two lanes. The use of ddATP and ddCTP are shown for illustration. It will be recognized that any combination of two different ddNTPs can be used. Advantageously, one is either ddATP or ddTTP and the other is either ddCTP or ddGTP. For dnF$_{1R}$ (right), a ddNTP and a different modified ddNTP (designated with *) are used simultaneously in one reaction followed by a denaturing electrophoresis in one lane. Again, for illustration ddATP and ddCTP* are shown. Dideoxy termination segments from downstream and upstream primers are identified by controls that visualize termination products from just one direction. In the example shown, the amplified region contains single-base mutations. Mutation one (M1) is an A→C mutation. (Symbols: →=downstream segment, ←=upstream segment). For dnF$_{2R}$, a segment is lost with ddATP from downstream primer in the first lane, and a second segment is gained with ddCTP from the downstream primer in the second lane. For dnF$_{1R}$, the extra and the absent segments also can be detected in one lane because mobility is retarded by the modified dideoxy terminator. Mutation two (M2) is a G→A mutation. A segment is gained with ddATP from downstream primer, the other segment is lost with ddCTP from upstream primer, which can be easily detected from downstream and upstream directions by both dnF$_{2R}$ and dnF$_{1R}$. The extra and missing termination segments at mutation sites are marked by arrows.

TABLE 1

Expected Dideoxy Sensitivity with Downstream and Upstream Primers and with ddATP and ddCTP Terminators

| | →A | →T | →G | →C |
|---|---|---|---|---|
| | ddA/ddC[b] | ddA/ddC | ddA/ddC | ddA/ddC |
| | DnStr, UpStr/ | DnStrUpStr/ | DnStrUpStr/ | DnStrUpStr/ |
| | DnStr, Upstr[b] | DnStr, UpStr | DnStr, UpStr | DnStr, UpStr |
| A→[a] | | −, +/0, 0 | −, 0/0, + | −, 0/+, 0[c,d,e] |
| T→ | +, −/0, 0 | | 0, −/0, + | 0, −/+, 0 |
| G→ | +, 0/0, − | 0, +/0, − | | 0, 0/+, − |
| C→ | +, 0/−, 0 | 0, +/−, 0 | 0, 0/−, + | |

[a]Wild-type base in the downstream direction.

[b]DnStr = downstream direction; UpStr = upstream direction orientation. The changes expected with a ddATP terminator are listed to the left of the slash, and changes with ddCTP terminator are listed to the right of the slash. Changes expected in the Sanger termination reaction proceeding in the downstream direction arelisted followed by changes in the upstream direction. For example, an A < G transition results in a lost segment when ddATP is used in the downstream direction, and an extra segment when ddCTP is used in the upstream direction. This is indicated by [−, 0/0, +].

[c]The underlined patterns of an extra and an absent segments from the same direction cannot be differentiated when ddATP and ddCTP are simultaneously used as terminators (dnF1R), but they can be picked up with ddATP and a large, modified ddCTP*.

[d]Every mutation is expected to produce one extra segment (+) and one absent segment (−). For each of the twelve possible sequence changes, the presence of an extra segment (+), an absent segment (−) or the absence of a change is indicated for each context.

The invention is further illustrated by the following examples, which are not intended to be limiting.

EXAMPLE 1

DnF of Two Regions of the Factor IX Gene

Figure 2A:
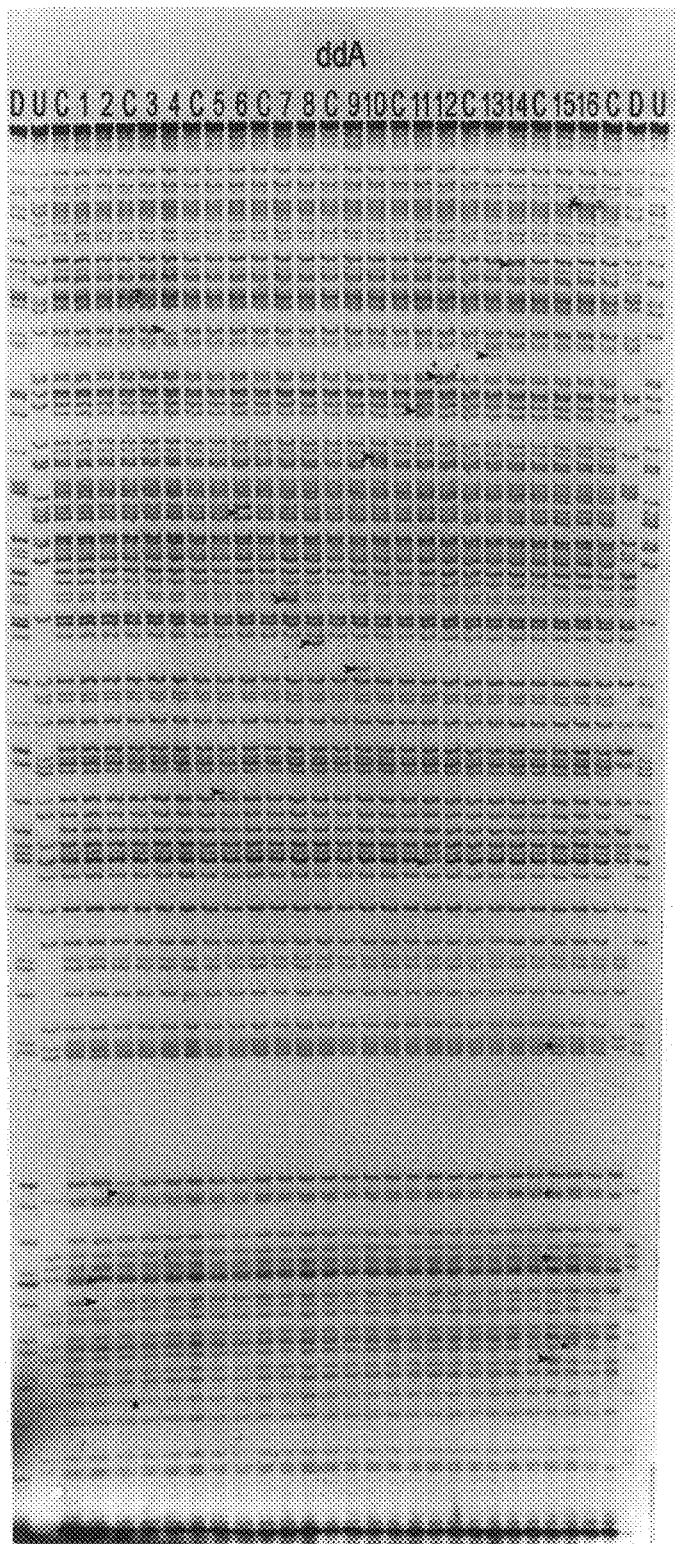
FIG. 2 illustrate gel electrophoresis fingerprint patterns resulting from $dnF_{2R}$ (A) and $dnF_{1R}$ (B) of a 1 kb region of exon 8 from the Factor IX gene.
Figure 2B:
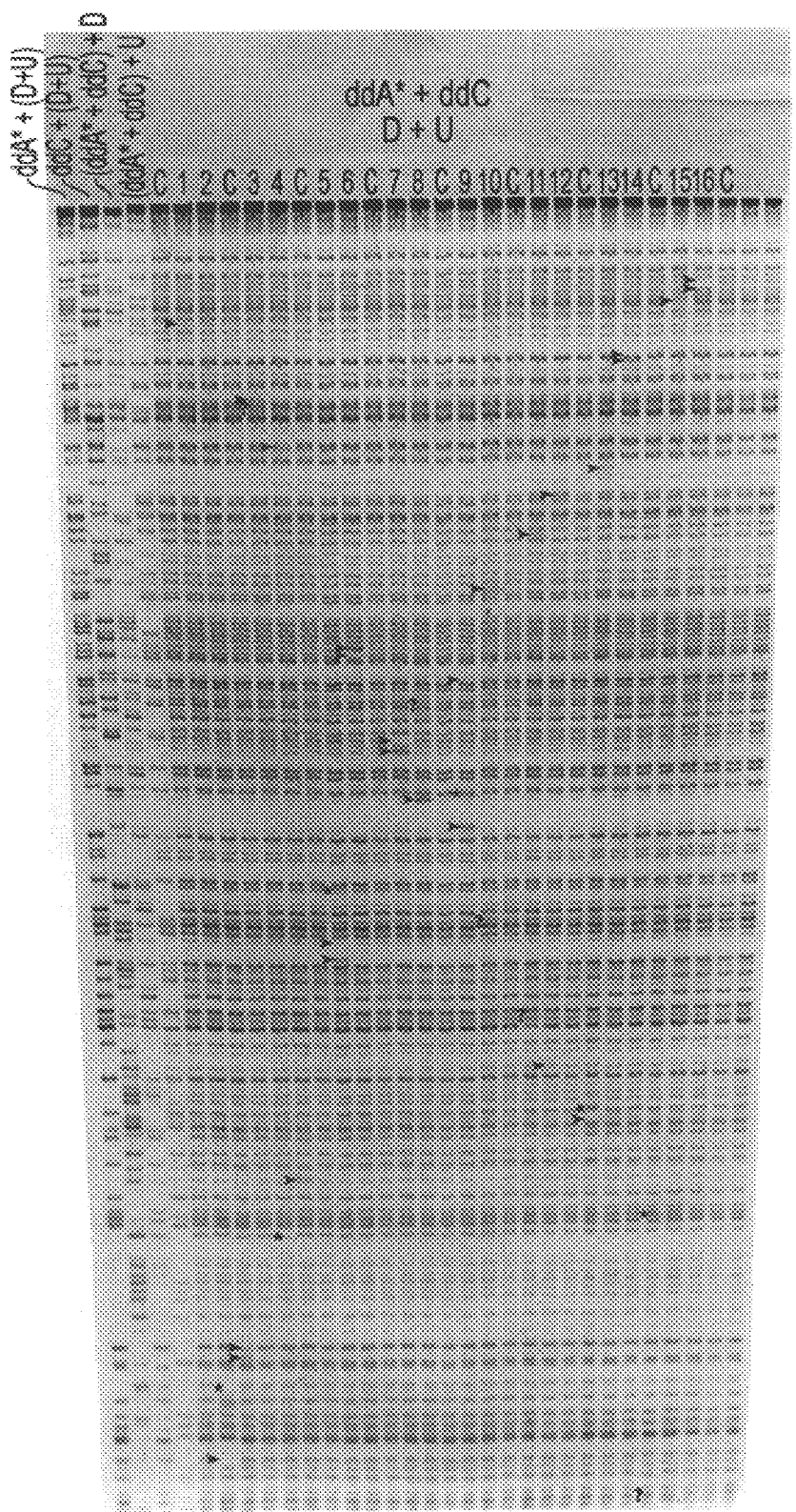

A 1-kb region of the exon 8 of the human Factor IX gene was amplified from genomic DNA with primers A and B. Cycle sequencing termination reactions with ddATP and ddCTP were electrophoresed through denaturing gels using materials and methods described below. Two regions within this segment were analyzed by either dnF$_{2R}$ or dnF$_{1R}$ in hemizygous males with hemophilia B. These samples also should reflect the situation when patients are homozygotes and when clones are analyzed. To localize the mutation, a pair of control reactions was performed with just the downstream or the upstream primer. All sixteen of the mutations in the samples were detected in both a 246-bp region (201 bp if the primer sequences are eliminated) and an adjacent 318-bp segment (284 bp if the primer sequences are eliminated). The results are shown in Table 2 below and in FIG. 2. In FIG. 2, gel A shows dnF$_{2R}$ with ddATP and primers C and D. Lane D: Wild-type control with a radio-labeled downstream primer. Lane U: with a radiolabeled upstream primer Lane C: with radiolabeled downstream and upstream primers. Lanes 1–16 are mutant samples and their types and positions are listed in Materials and Methods. →=an extra or a lost segment at mutation site, ?=false negative and and *=shifted segment due to SSCP effect. Gel B shows the results of dnF$_{1R}$ analysis with ddATP and fluorescence-labeled ddCTP* and primers C and D. Same as in Gel A.

Although every mutation is expected to result in one extra termination segment and one lost termination segment, in practice, one or another segment may not be visualized. The extra termination segment may migrate in the same position as a termination segment from the opposite direction. This should occur approximately 25% of the time. In some cases, this will be manifested by a clear difference in intensity of that segment relative to those in the neighboring lanes. However, the great variation in termination efficiency from base to base with Taq DNA polymerase implies that a clear-cut intensity difference will not always be seen. In addition, occasional termination segments are too weak to be visualized on a gel. Thus, extra segments that do not overlap a termination segment in the opposite direction may not be visualized. For dnF$_{1R}$, overlapping segments are expected about 60% of the time (i.e., for a random sequence of 50% G+C, the probability of an extra segment produced by ddATP not overlapping a segment produced by ddATP with the opposite primer or ROX-ddCTP with either primer is $(\frac{3}{4})^3 = 0.42$). An analysis of the extra and lost segments in the above experiments revealed the expected frequency of unequivocal extra segments and lost segments for dnF$_{2R}$. For reasons that are unclear, the frequency was higher than expected for dnF$_{IR}$ (56% of 64 extra or absent segments). In dnF$_{IR}$, the ten lost segments and three extra segments that could not be detected resulted from a combination of compression in the upper part of the gel and low intensity of

TABLE 2

Summary of Experiments

|   | Gene[a] | Segment Size[b](bp) | G & C Control(%) | Type of Experiment | Zygosity | No. of Mutations | dnF$_{2R}$ Detection | dnF$_{1R}$ Detection |
|---|---|---|---|---|---|---|---|---|
| 1 | FIX | 248 | 44 | Known | Hemizygote | 16 | 16 | 16 |
| 2 | FIX | 318 | 41 | Known | Hemizygote | 16 | 16 | 16 |
| 3 | FIX | 248 | 44 | Blinded | Hemizygote | 24(48) | 24 | 24 |
| 4 | FIX | 248 | 44 | Blinded | Heterozygote | 12(18) | 10[c] | 11[c] |
| 5 | FIX | 318 | 41 | Blinded | Heterozygote | 19(30) | 14[d] | 14[d] |
| 6 | FIX | 417–557 | 52–62 | Screening | Heterozygote |  | 4 |  |

[a]FIX = Human factor IX gene; TNFα = Human tumor necrosis factor a gene in which four regions were screened in patient samples.
[b]The screening regions are assigned between the 5' ends of the downstream and upstream primers.
[c]In the 248-bp segment of the factor IX gene, two and one heterozygous mutations were missed due to weakly terminated segments by dnF$_{2R}$ and dnF$_{1R}$, respectively.
[d]In the 318-bp segment of the factor IX gene, five heterozygous mutations were missed due to weakly terminated segments and poor separation on the upper part of the gel by dnF$_{2R}$ and dnF$_1$, respectively.
[e]The gene was screened in four regions with a G + C content ranging from 57% to 62%.
[f]Known = the person performing the analysis knew which samples had mutations and which samples did not; blinded = the analysis was performed without knowledge of which samples contained mutations; screening = the gene was analyzed in a prospective manner in search of mutations.

particular Taq termination products (FIG. 2, see "?"). In addition to the above, a few mutant-containing termination products were also detected by SSCP-type mobility shifts, which presumably resulted from residual secondary structure (FIG. 2, see "*"). In dnF$_{2R}$, thirteen mobility shifts were seen with eight of the mutations, and, in dnF$_{IR}$, thirteen mobility shifts were seen with eleven of the mutations.

Materials and Methods

Oligonucleotides

All the oligonucleotides are specific for the human factor IX gene. The abbreviated informative names (9,11) are listed below:

A: I7(30646)-34D; B: E8(31645)-31U;
C: E8(30880)-21D; D: E8(31125)-16U;
E: E8(31112)-16D; and F: E8(31429)18U.

As an example of the nomenclature, I7(30646)-34D is an oligonucleotide in which the 5' end begins in intron 7 at bp 30646 [numbering as described in Yoshitake et al. (13)]. The length of the oligonucleotide is 34 bases, and the orientation is in "downstream" (D), i.e., in the direction of transcription. The precise sizes and locations of the amplified segments and the dideoxy termination reactions can be obtained from the in informative names.

Mutations

For the analysis, the genomic DNA with the following mutations in the human factor IX gene were analyzed from patients with hemophilia B. The sample numbers and associated mutations correspond to the lane numbers for FIG. 2 with primers C and D. 1: A30918G; 2: C30928A; 3: T30936G; 4: T30945C; 5: C30973A; 6: T30985G; 7: G31001T; 8: C31008T; 9: C31012T; 10: G31029A; 11: T31039A; 12: G31047A; 13: G31052A; 14: C31077A; 15: C31091T; and 16: C31096A [numbering as described in Yoshitake et al. (13)]. The following are utilized with primers E and F: 1: T31166A; 2: G31175A; 3: G31187T; 4: G31203T; 5: G31211T; 6: G31218A; 7: T31253G; 8: A31227G; 9: T31274A; 10: A31281G; 11: G31289A; 12: A31301G; 13: T31311C; 14: C31317A; 15: T31340C; and 16: C31356A.

PCR and Taq Cycling Sequencing

A 1-kb region of the exon 8 was amplified with primers A and B (4). Taq cycle sequencing was performed according to Innis et al. (3) with γ$^{33}$P [ATP]-labeled primers (Amersham, Arlington Heights, Ill., USA). Denaturation was at 95° C. for 15 s, annealing was at 55° C. for 30 s and elongation was at 68° C. for 4 min for a total of 20 cycles for primers C and D to screen a 246-bp region or for primers E and F to scan a 318-bp region. The sequencing mixture contained a total volume of 8 μL: 80 mM Tris-HCI, pH 9.0, 2.0 mM MgCl2, 20 mM (NH$_4$)$_2$SO$_4$, 10 RM of each dNTP, 1 U of AmpliTaqQ9 (Perkin-Elmer, Norwalk, Conn., USA), 10 ng of amplified DNA and 0.05 RM each of cycle sequencing primers C and D or E and F. In dnF$_{2R}$, each sequencing reaction contains 400 μM ddATP or 200 μM ddCTP as terminator; while in dnF$_{IR}$, the sequencing reaction contained 200 μM ddATP and 6000 μM ROX-ddCTP or (ddCTP*; PE Applied Biosystems, Foster City, Calif., USA) 100 μM of ddCTP and 2250 μM of fluorescence labeled ddATP (ddATP*). After Taq cycle sequencing, 16 μL of stop/loading buffer (7 M urea, 50% formamide and 2 mM EDTA) were added to each tube. The extension efficiency with the two opposite primers is 5–10-fold greater than that with either single primer.

Denaturing Electrophoresis

Electrophoreses of 7 M urea and 6% Long Ranger™ gels (0.4-mm thickness; FMC BioProducts, Rockland, Me., USA) were performed with a TBE buffer (50 mM Trisborate, 1 mM EDTA, pH 8.3) at 65 W constant power. After pre-electrophoresis for 30 min, 1.5 μL of samples were loaded for 2 h, and the temperature on the plate was kept at 45° C. The gel was dried and subjected to Kodak BioMax MR film for autoradiography (Scientific Imaging Systems [Eastman Kodak], New Haven. Conn. USA).

Analysis of Resolution

Absent termination segments or extra segments were scored by visual analysis for the presence of unequivocal migration and intensity changes in relation to normal controls. If segments were crowded or compressed, a clearly distinguishable increase in the "complexity" of the segments or a 50% increase in segment intensity was judged to have an extra segment; and a reduction of complexity or a 50% reduction in segment intensity was judged to have an absent segment. A normal control was loaded every three lanes, so that a mutant sample always was immediately adjacent to a normal sample.

Results

Blinded Analyses

Three blinded analyses were performed (Table 2). For each analysis, a mixture of mutant and wild-type samples were encoded such that the individual performing the analysis had no knowledge of which sample had mutations or how many total mutations there were. In the first blinded analysis, 48 samples were analyzed within the 248-bp region. There were 24 mutations not previously analyzed, and all were detected. There were no false positives. Additional blinded analyses were performed with heterozygote samples. Of 18 samples, 12 contained mutations within the 248-bp region. Two of these mutations were missed with $dnF_{2R}$, and one was missed with $dnF_{IR}$. Within the 318-bp region, a blinded analysis with 19 heterozygous mutations among 30 samples revealed that five mutations were missed. There were no false positives. The characteristics of the bands are summarized in Table 3 below.

TABLE 3

| Type | Segment Size | Mutation-induced Bands | Detected by Separation | Intensity Only | Not Detected |
|---|---|---|---|---|---|
| $dnF_{2R}$ | 248 bp | Extra (+) | 12 | 4 | 0 |
|  |  | Lost (−) | 12 | 3 | 1 |
|  | 318 bp | Extra (+) | 13 | 3 | 0 |
|  |  | Lost (−) | 15 | 0 | 1 |
| $dnF_{1R}$ | 248 bp | Extra (+) | 9 | 6 | 1 |
|  |  | Lost (−) | 10 | 2 | 4 |
|  | 318 bp | Extra (+) | 8 | 6 | 2 |
|  |  | Lost (−) | 9 | 1 | 6 |

EXAMPLE 2
The TNFα Gene; Four Regions with High G+C $DnF_{2R}$ was utilized to detect mutations in tumor necrosis factor α, a gene with high G+C content of 52%–62%, in which ddF and bi-ddF smeared when performed at room temperature in the absence of denaturing reagents. Sequencing reaction and electrophoresis materials and methods were essentially the same as in Example 1. Seventy-eight patients with multiple sclerosis were screened. The promoter region and the four exons and their flanking splice junctions were analyzed (total 1944 bp of sequence), and four heterozygous sequence variants were found, including three single-base substitutions and a one-base insertion (Table 2). These variants are reported elsewhere (12).

$DnF_{IR}$ involves about half the work of $dnF_{2R}$, but the pattern contains about two times as many segments. In blinded analyses, $dnF_{IR}$ was as sensitive as $dnF_{2R}$, so it seems to be the preferred technique. However, $dnF_{IR}$ is less forgiving; a suboptimal gel is more likely to lead to false-negative results. In summary, $dnF_{2R}$ and $dnF_{IR}$ are simple and effective methods for mutation scanning.

For mutations in hemizygous, homozygous and cloned templates, $dnF_{2R}$ or $dnF_{IR}$ can detect virtually all mutations (56 of 56 tested mutations) with about one-half ($dnF_{2R}$) or one-quarter ($dnF_{IR}$) of the work, respectively, of sequencing. The sensitivity of $dnF_{2R}$ and $dnF_{IR}$ for heterozygotes may be improve by (i) reducing the urea concentration to encourage more mobility shifts due to residual secondary structure while keeping most segments tightly focused for optimal resolution; (ii) using dideoxy terminators that more optimally retard mobility, (iii) using sequencers in which segments must migrate at a defined distance to the detector (e.g., the PE Applied Biosystems or Pharmacia Biotech fluorescent sequencers) and (iv) using thermo sequencers (Amersham) or TaqFS DNA polymerase (PE Applied Biosystems) to produce more even intensity termination segments.

The invention has been described by reference to certain preferred embodiments. Those skilled in the art will appreciate that various modifications and improvements may be made which fall within the scope of protection of the appended claims.

REFERENCES

1. Blaszyk, H., A. Hartmann, J. J. Schroeder R. M. McGovern, S. S. Sommer and J. S. Kovach. 1995. Rapid and efficient screening for p53 gene mutations by dideoxy fingerprinting (ddF). BioTechniques 18:256–260
2. Haavik, J., H. Nishino, Q. Liu and S. S. Sommer, 1996. Bi-directional dideoxyy fingerprinting (Bi-ddF): rapid and efficient screening for mutations in the Big Blue transgenic mouse mutation detection system. BioTechniques 20:988–994.
3. Innis, M. A., K. B. Myambo, D. H. Gelfand and M. A. D. Brow. 1988. DNA sequencing with *Thermus aquaticus* DNA polymerase and direct sequencing of polymerase chain reaction-amplified DNA. Proc. Natl Acad. Sci. USA 85:9436–9440
4. Liu, Q., J. Feng and S. S. Sommer. 1996 Bidirectional dideoxy fingerprinting (Bi-ddF): a rapid method for quantitative detection of mutations in genomic regions of 300–600 bp. Hum. Mol. Genet. 5:107–114.
5. Liu, Q. and S. S. Sommer. 1994. Parameters affecting the sensitivities of dideoxy fingerprinting and SSCP. PCR Methods Appl. 4:97108.
6. Livak, K. J., E W. Hobbs and R J. Zagursky. 1992. Detecton of single base differences using biotinylated nucleotides with very long linker arms Nucleic Acids Res. 20:4831 4837.
7. Orita, M., H. Iwahana, H. Kanazawa, K. Hayashi and T. Sekiya. 1989. Detection of polymorphisms of human DNA by gel electrophoresis as single-strand conformation polymorphisms. Proc. Natl. Acad. Sci. USA 86:2766–2770.
8. Prober, J. M., G. L. Trainor, R J. Dam, E W. Hobbs, C. W. Robertson, R. J. Zagursky A. J. Cocuzza, M. A. Jensen and K. Baumeister. 1987. A system for rapid DNA sequencing with fluorescent chain-terminating dideoxynucleotides. Science 238:336–341.
9. Sarkar, G. and S. S. Sommer. 1989. Access to an mRNA sequence or its protein product is not limited by tissue or species specificity. Science 244:331–334.
10. Sarkar, G., H. Yonn and S. S. Sommer. 1992. Dideoxy fingerprinting (ddF): a rapid and efficient screen for the presence of mutations Genomics 13:441–443
11. Sommer S. S. and E. L. Vielhaber. 1994. Phage promoter-based methods for sequencmg and screening for mutations, p. 214–221. In K. Mullis, F. Ferre and R. A. Gibbs (Eds ) The Polymerase Chain Reaction. Birkhauser, Boston
12. Weinshenker, B. G., D. W. Wingerchuk, O. Liu, A. S. Bissonnett, D. J. Schaid and S. S. Sommer. 1997. Genetic variation in the tumor necrosis factor cs gene and the outcome of multiple sclerosis. Neurology 49:378–385.
13. Yoshitake, S., B. G. Schach, D. C. Foster E. W. Davie and K. Kurachi. 1985. Nucleotide sequence of the gene for human factor IX (anti-hemophilic factor B). Biochemistry 24:3736–3750

What is claimed is:
1. A denaturation fingerprinting method for detecting mutations in a nucleic acid segment which comprises
 subjecting the nucleic acid segment to bidirectional sequencing using oppositely oriented primers that bound the segment and two different dideoxynucleotide terminators in a single reaction,
  wherein one of the dideoxynucleotide terminators is either ddATP or ddTTP and the other is either ddGTP or ddCTP, and wherein one of the dideoxynucleotide terminators is modified so as to alter the electrophoretic mobility of fragments containing a residue of the modified dideoxynucleotide terminator relative to fragments containing the corresponding unmodified dideoxynucleotide terminator, and separating the resulting fragments by denaturing electrophoresis in one lane to produce a fingerprint pattern.

2. The method of claim 1 wherein the modified dideoxynucleotide is modified by a fluorescent dye label.

* * * * *